United States Patent [19]

Illig

[11] Patent Number: 5,573,749
[45] Date of Patent: Nov. 12, 1996

[54] NANOPARTICULATE DIAGNOSTIC MIXED CARBOXYLIC ANHYDRIDES AS X-RAY CONTRAST AGENTS FOR BLOOD POOL AND LYMPHATIC SYSTEM IMAGING

[75] Inventor: Carl R. Illig, Phoenixville, Pa.

[73] Assignee: Nano Systems L.L.C., Collegeville, Pa.

[21] Appl. No.: 401,397

[22] Filed: Mar. 9, 1995

[51] Int. Cl.$^6$ .......................... A61K 49/04; C07C 69/96; C07C 63/68
[52] U.S. Cl. .......................... 424/9.45; 558/276; 562/887
[58] Field of Search .......................... 424/9.45; 558/276; 562/887

[56] References Cited

U.S. PATENT DOCUMENTS

| | | | |
|---|---|---|---|
| 3,097,228 | 7/1963 | Larsen | 260/471 |
| 4,607,123 | 8/1986 | Schuster et al. | 564/153 |
| 5,318,767 | 6/1994 | Liversidge et al. | 424/4 |

FOREIGN PATENT DOCUMENTS

| | | |
|---|---|---|
| 0498482A2 | 1/1992 | European Pat. Off. . |
| 3407473 | 9/1985 | Germany . |
| 8501727 | 4/1985 | WIPO . |

OTHER PUBLICATIONS

Swanson et al, "Pharmaceuticals in Medical Imaging", 1990, MacMillan Publishing Company.
Chemical Abstract 149397–07–9 (1994).
Chemical Abstracts 105: 60940, 1985.

Primary Examiner—S. Mark Clardy
Assistant Examiner—Mary C. Cebulak
Attorney, Agent, or Firm—Rudman & Balogh

[57] ABSTRACT

This invention relates to methods of x-ray diagnostic imaging the blood pool, liver, spleen, and/or lymph system of a mammal comprising administering a contrast effective amount of a mixed carbonic anhydride as a contrast agent having the structure

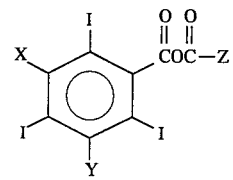

X is H, NR$^1$R$^2$ or CONR$^1$R$^3$,
R$^1$ is H or alkyl
R$^2$ is COR$^3$
R$^3$ is H, alkyl or aryl
Y is NR$^1$R$^2$ or CONR$^1$R$^3$ and
Z is alkyl, aryl or aralkyl.

This invention further relates to novel mixed carboxylic anhydride contrast agents having the above structure to x-ray contrast compositions comprising such agents, and to methods of x-ray diagnostic imaging utilizing such agents.

7 Claims, No Drawings

NANOPARTICULATE DIAGNOSTIC MIXED CARBOXYLIC ANHYDRIDES AS X-RAY CONTRAST AGENTS FOR BLOOD POOL AND LYMPHATIC SYSTEM IMAGING

FIELD OF INVENTION

This invention relates to methods of x-ray diagnostic imaging the blood pool, liver, spleen, and/or lymph system of a mammal employing particulate mixed carboxylic anhydrides as a contrast agent, and to certain novel mixed carboxylic anhydrides useful as contrast agents in x-ray contrast compositions and methods of diagnostic imaging.

BACKGROUND OF THE INVENTION

X-ray imaging is a well known and extremely valuable tool for the early detection and diagnosis of various disease states in the human body. The use of contrast agents for image enhancement in medical x-ray imaging procedures is widespread. An excellent background on iodinated and other contrast agents for medical imaging is provided by D. P. Swanson et al, *Pharmaceuticals in Medical Imaging*, 1990, MacMillan Publishing Company.

Chemical Abstract 149397-07-9 describes an aryl having two aryl groups having the formula:

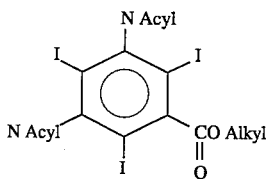

This compound is not a mixed carboxylic anhydride and no mention is made of its potential use as an x-ray contrast agent.

U.S. Pat. No. 3,097,228 describes derivatives of 2,4,6-triiodobenzoyloxyalkanoic acids having the structure

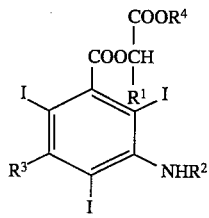

wherein $R^1$ is H or lower alkyl; $R^2$ is H or lower alkanoyl; $R^3$ is H or lower alkanoylamino and $R^4$ is lower alkyl. The agents are useful as x-ray contrast agents for visualizing the gall bladder (cholecystography) when administered orally, in the free acid form or in the form of a non-toxic salt, or intravenously, in the form of water soluble, non-toxic salt. Example 15 therein describes ethyl 2-(3,5-diacetamido- 2,4,6-triiodobenzoyloxy)hexanoate, i.e.,

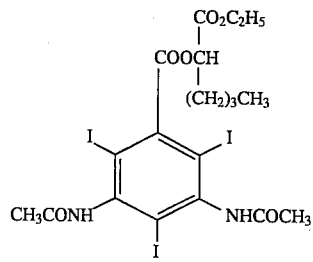

Bacon et al, commonly assigned U.S. Pat. application Ser. No. 07/990,987 filed Dec. 16, 1992 describes iodinated aroyloxy esters which are useful as contrast agents in x-ray imaging compositions and methods. However, all of the compounds described by Bacon et al feature an ester group linked through a $C_2$ or higher alkylene group to another ester group on an iodinated aromatic ring.

EP-A 498,482 describes nanoparticulate x-ray contrast compositions which have proven to be extremely useful in medical imaging. The compositions comprise particles of an organic x-ray contrast agent and a surface modifier absorbed on the surface thereof and have an effective average particle size of less than 400 nm. The agents can be delivered to a specific tissue or fluid site, e.g., the blood pool, liver, spleen, kidney or lymph nodes. Example 8 therein describes a formulation comprising ethyl 2-(3,5-bis(acetylamino)- 2,4,6-triiodobenzoyloxy)butyrate, i.e.,

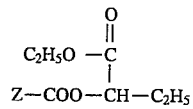

wherein (Z)-COO is the residue of diatrizoic acid.

However, it has been discovered that ethyl 2-(3,5-bis(acetylamino)-2,4,6-triiodobenzoyloxy)butyrate exhibits multiple crystal forms, i.e., polymorphism, e.g., when recrystallized from various solvents. The reasons for this behavior are not completely understood but, in any event, multiple crystal forms are disadvantageous for a variety of reasons. For example, the presence of multiple crystal forms renders scale up problematic due to the lack of reproducibility of the results obtained, including, e.g., in chemical manufacturing and in the milling process. Additionally, it has been found that nanoparticulate formulations of ethyl 2-(3,5-bis(acetylamino)-2,4,6-triiodobenzoyloxy)butyrate do not exhibit good stability during autoclaving, i.e., conventional heat sterilization.

Consequently, to be useful as x-ray contrast agents, the agents must possess stability prior to and during the imaging period and then be cleared from the body rapidly afterward. It would be desirable to provide a poorly soluble x-ray contrast agent having the potential to hydrolyze to safe, tolerated metabolic end products.

SUMMARY OF THE INVENTION

We have discovered that certain mixed carboxylic anhydrides exhibit reproducibly consistent crystal morphology during manufacture and purification and hydrolyze to safe, tolerated metabolic end products and thus are particularly amenable to use as particulate contrast agents for use in methods of x-ray diagnostic imaging the blood pool, spleen, liver, and lymphatic system of a mammal. In a composition of matter aspect, we have discovered and synthesized novel mixed carboxylic anhydrides which are useful as contrast agents in x-ray diagnostic imaging compositions and methods.

More specifically, in accordance with this invention, there is provided a method of medical x-ray diagnostic imaging which comprises administering to the blood pool, liver, spleen, or lymph system of a mammal a contrast-effective amount of a particulate diatrizoxy ester contrast agent having structure I.

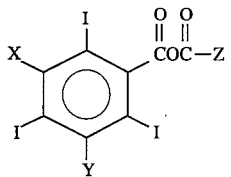

wherein

X is H, $NR^1R^2$ or $CONR^1R^3$, $R^1$ is H or alkyl $R^2$ is $COR^3$ $R^3$ is H, alkyl or aryl Y is $NR^1R^2$ or $CONR^1R^3$ and Z is alkyl, aryl or aralkyl.

In another aspect, there are provided novel mixed carboxylic anhydrides having structure I above. This invention further provides an x-ray contrast composition comprising such novel compounds and a method for medical x-ray diagnostic imaging which comprises administering to a mammal an effective contrast-producing amount of the above-described x-ray contrast composition.

It is an advantageous feature of this invention that methods of x-ray diagnostic imaging the blood pool, liver, spleen, and lymphatic system are provided employing an x-ray contrast composition featuring a mixed carboxylic anhydride which exhibits a consistent crystal morphology during purification and thus is particularly amenable to reproducible scale up and hydrolyzing to a safe, tolerated metabolic end product.

It is a particularly advantageous feature of this invention that x-ray contrast compositions are provided for blood pool, liver, spleen, and lymphatic system imaging which exhibit improved safety in that these contrast agents will clear from the body in a very short amount of time, thus giving maximum efficacy with maximum safety features.

Still another advantageous feature of this invention is that novel mixed carboxylic anhydrides are provided which find particular utility as particulate x-ray contrast agents.

DESCRIPTION OF PREFERRED EMBODIMENTS

In structure I above,

X is H, $NR^1R^2$ or $CONR^1R^3$.

$R^1$ is H or a linear or branched alkyl preferably containing from 1 to 16 carbon atoms such as methyl, ethyl, propyl, isopropyl, butyl, pentyl, hexyl and the like, fluoroalkyl, the alkyl portion of which is as defined above and containing from 1 to (2n+1) fluorine atoms (where n is the number of carbon atoms in the alkyl group, such as trifluoromethyl) cycloalkyl, preferably containing 3 to 8 carbon atoms such as cyclopropyl, cyclobutyl, cyclopentyl and cyclohexyl and substituted alkyls such as alkyls substituted with hydroxyls, alkoxyls ($OR^1$) or X and the like.

$R^2$ is an acyl group containing from 2 to 16 carbon atoms such as $COCH_3$, $COC_3H_7$, $COC_4H_9$, and including hydroxy substituted acyl groups such as $COCH_2OH$, $COCH(OH)CH_3$, $COCH(OH)CH_2OH$ and the like.

$R^3$ is H, an alkyl preferably containing from 1 to 16 carbon atoms such as described above, hydroxy-substituted alkyl containing 1 to 16 carbon atoms and up to (n–1) hydroxyls where n is the number of carbon atoms, aryl, preferably containing from 6 to 10 carbon atoms such as phenyl and napthyl.

X is most preferably $NHCOCH_3$.

Y is $NHCOCH_3$.

$NR^1R^2$ or $CONR^1R^3$ wherein $R^1$, $R^2$ and $R^3$ are as described above. Y is most preferably $NHCOCH_3$.

Z is a linear or branched alkyl, preferably containing from 1 to 20 carbon atoms, more preferably 6 to 18 carbon atoms such as methyl, ethyl, propyl, isopropyl, butyl, pentyl, hexyl and the like, fluoroalkyl, the alkyl portion of which is defined above and containing from 1 to (2n+1) fluorine atoms (where n is the number of carbon atoms in the alkyl group), such as trifluoromethyl, cycloalkyl, preferably containing from 3 to 8 carbon atoms such as cyclopropyl, cyclobutyl, cyclopentyl, and cyclohexyl, aryl, preferably containing from 6 to 10 carbon atoms, such as phenyl and naphthyl; and aralkyl preferably containing from 7 to 12 carbon atoms; such as benzyl.

The compound of this invention can be prepared by acylation of the iodinated benzoate having the structure

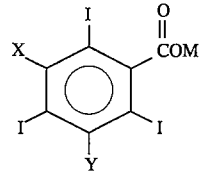

where X and Y are as defined above and M is selected from the group consisting of Na, K, Ca and $NR^3_4$ wherein $R^3$ is alkyl having 1 to 4 carbon atoms such as methyl, ethyl, propyl, isopropyl and butyl and the like or aralkyl preferably containing from 7 to 10 carbon atoms and as benzyl, with an acid chloride or anhydride having the structure

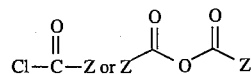

wherein Z is as described above.

The reaction can be run with any suitable non-nucleophilic solvent where both starting components have full or partial solubility. Preferred solvents include N,N-dimethylformamide and N,N-dimethylacetamide. The iodinated benzoate starting material is preferably derived from diatrizoic acid, metrizoic acid, iothalamic acid, iodipamide acid and the like.

The iodinated compounds can contain substituents which do not deleteriously affect the contrast-enhancing capability of the compound. For example, the alkyl, cycloalkyl, aryl, aralkyl and alkoxy groups in structure I above can be unsubstituted or substituted with various substituents which do not adversely affect the stability or efficacy of the compounds as x-ray contrast agents such as alkyl, cycloalkyl, aryl, aralkyl, alkoxy, hydroxy, acyloxy, halogen, such as chlorine, bromine and iodine, acylamino, carboalkoxy, carbamyl and the like.

When used as an x-ray contrast agent, the compound of this invention preferably comprises at least about 30%, more preferably at least 35%, and most preferably at least 40% iodine by weight.

In preferred embodiments, the compounds of this invention can be formulated into particulate x-ray contrast compositions, preferably nanoparticulate x-ray contrast compositions, as described in commonly-owned EP-A 498,482. Preferred compounds exhibit a melting point of greater than 150° C. Such nanoparticulate compositions can be prepared by dispersing the compounds of the invention in a liquid dispersion medium, and wet grinding the compound in the presence of rigid grinding media and a surface modifier to form the nanoparticles. Alternatively, the surface modifier can be contacted with the compound after attrition. Preferred surface modifiers include nonionic surfactants.

In preferred embodiments, the surface modifier is a high molecular weight nonionic surfactant. Preferred surfactants include poloxamers such as Pluronic™ F68 and F108, which are block copolymers of ethylene oxide and propylene oxide, poloxamines, such as Tetronic™ 908, which is tetrafunctional block copolymer derived from sequential addition of propylene oxide and ethylene oxide to ethylenediamine, and dialkyl esters of sodium sulfosuccinic acid, such as dioctylsulfosuccinate sodium (DOSS). The concentrations of the surface modifier can vary from about 0.1–75%, preferably 1–60%, and more preferably 5–25% by weight based on the total combined weight of the contrast agent and surface modifier.

In preferred embodiments, the x-ray contrast compositions in the form of surface modified nanoparticles can be associated with a cloud point modifier to further enhance stability during steam heat autoclaving, i.e., the cloud point modifier can reduce particle aggregation during heat sterilization. Preferred cloud point modifiers include nonionic cloud point modifiers, such as polyethylene glycols such as PEG 400, propylene glycol, ethanol, hydroxypropylcyclodextrin and glycerol; ionic cloud point modifiers, such as those described in U.S. Pat. No. 5,298,262 including dialkylesters of sodium sulfosuccinic acid such as the dioctylester of sodium sulfosuccinic acid (DOSS); and charged phospholipids, such as a diacylphosphatidyl glycerol, e.g., dimyristoylphosphatidyl glycerol. The cloud point modifier can be present in an amount of 0.005–50%, preferably 0.01–30% and more preferably 0.05–20% by weight based on the total weight of the x-ray contrast composition.

The x-ray contrast compositions of this invention comprise the above-described compounds, preferably in the form of particles, and a physiologically acceptable carrier therefor. For example, the particles can be dispersed in an aqueous liquid which serves as the carrier for the x-ray contrast agent. Other suitable carriers include liquid carriers such as mixed aqueous and nonaqueous solvents, such as alcohol; gels; gases, such as air; and powders.

The x-ray contrast compositions can comprise from about 1–99.9%, preferably 2–45% and more preferably 10–30% by weight of the above-described particles, the remainder of the compositions being the carrier, additives and the like. Compositions up to about 100% by weight of the particles are contemplated when the composition is in a lyophilized form.

The dose of the contrast agent to be administered can be selected according to techniques known to those skilled in the art such that a sufficient contrast enhancing effect is obtained. Typical doses can range from 20 to 450 mg of iodine per kilogram of body weight of the subject for many imaging applications. For some applications, e.g., lymphography, lower doses, e.g., 0.5–20 mg I/kg, can be effective. For blood pool imaging, the dose can range from 50 to 450 mg of iodine per kilogram of body weight and preferably from 100 to 250 mg of iodine per kilogram of body weight. For liver and spleen the dose can be from 50 to 300 mg iodine per kg of body weight.

The x-ray contrast compositions can contain one or more conventional additives used to control and/or enhance the properties of the x-ray contrast agent. For example, thickening agents such as dextran or human serum albumin, buffers, viscosity regulating agents, suspending agents, peptizing agents, anticlotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

A method for diagnostic imaging for use in medical procedures in accordance with this invention comprises administering to the body of a test subject in need of an x-ray an effective contrast producing amount of the above-described x-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays to produce an x-ray image pattern corresponding to the presence of the contrast agent. The image pattern can then be visualized. For example, any x-ray visualization technique, preferably, a high contrast technique such as computed tomography, can be applied in a convention manner. Alternatively, the image pattern can be observed directly on an x-ray sensitive phosphor screen-silver halide photographic film combination.

The compositions of this invention can be administered by a variety of routes depending on the type of procedure and the anatomical orientation of this tissue being examined. Suitable administration routes include intravascular (arterial or venous) administration by catheter, intravenous injection, rectal administration, subcutaneous administration, intramuscular administration, intralesional administration, intrathecal administration, intracisternal administration, oral administration, administration via inhalation, administration directly into a body cavity, e.g., arthrography, and the like.

In addition to preferred applications, i.e., for blood pool and lymph node imaging, the x-ray contrast compositions of this invention are also expected to be useful as contrast agents for any organ or body cavity. For example, the compositions of this invention are expected to be useful as anglographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The following examples further illustrates the invention.

EXAMPLE 1

General procedure for preparation Of carboxylic anhydrides:

To a solution of 200 mmol of the iodinated benzoate sodium salt in 350 mL of DMF can be added 220 mmol of the appropriate carboxylic chloride or anhydride. After stirring the mixture at a temperature in the range of −10° C. to 60° C. from one to 24 hour, the mixture can be poured into 3–4 L of water, dried under suction and dried under vacuum over $P_2O_5$ from 20°–70° C. Further purification, if necessary, can be carried out by pouring a 25–50% (w/v) solution of the product in DMF into 10 volumes of water, filtering and drying as before.

EXAMPLES 2–4

Preparation of Nanoparticulate Compound 2 Contrast Agents with Pluronic F68, Pluronic F108, or Tetronic T-908

Compound 1 can be added to each of 3×1.5 oz brown glass bottles containing approximately 12 ml of zirconium silicate (1.1 media.) beads in an amount sufficient to be 15% (w/v) of the final suspension. Bottle A can contain 3% (w/v) Pluronic F-68. Bottle B can contain 3% (w/v) Pluronic F108. Bottle C can contain 3% (w/v) Tetronic T-908. The resulting suspensions were milled on a roller mill at approximately 150 rpm for a total of 9 days.

EXAMPLES 5–6

Preparation of Nanoparticulate Compound 2 in Table I Contrast Agent with Pluronic F108 and Blood Pool Imaging 15% of Compound 2 can be milled with 4% Pluronic F-108 in the presence of zirconium silicate (1.1 mm dia) beads for 3 days under aseptic conditions. No additional salts or surfactants are added.

This sample can be examined for imaging efficacy as follows. The sample can be injected into white New Zealand rabbits at a dose of 3 ml/kg as a slow bolus injection. At times of 5, 15, 30, 60 and 120 min. post injection, the opacification of the liver, spleen, and blood pool as measured in the aorta and within the left ventricle can be determined by computed tomography (CT) using Toshiba 900S Imager CT scanner and associated software. Results from this analysis should indicate that formulation of Compound 2 should show excellent blood pool opacification in excess of 30 min. followed by very good liver and very good spleen opacification. Imaging at 24 hours post injection should show complete clearance from the blood with partial clearance from the liver and spleen.

EXAMPLE 7

Preparation of an Autoclavable Formulation of Nanoparticulate Compound 2 in Table I Contrast Agent with Pluronic F108 and PEG 400 and Lymphography Imaging Compound 2 can be milled with zirconium silicate (1.1 mm dia) beads in the presence of Pluronic F-108 for 3 days. At this point, sterile PEG 400 can be added to the suspension such that at completion, the formulation contained 15% (w/v) WIN 70146, 3% (w/v) Pluronic F-108, and 10% (w/v) PEG 400. This formulation can then be autoclaved under standard conditions, i.e., 121° C. for 20 min., resulting in a final nanoparticulate size of less than 1000 nm.

This formulation can be evaluated for both blood pool and lymphographic imaging in New Zealand White Rabbits using the above-described protocol (3 ml/kg) for blood pool imaging and 2 injections (0.25 ml) per paw for lymphography. The results should indicate that Compound 2 is capable of blood pool opacification to at least 30 min. and is an excellent lymphography agent affording high levels of opacification. Scanning can be carried out using a Toshiba 900S Imaginer CT scanner and image density calculated from iodinated standards imaged simultaneously with the animals.

The invention has been described in detail with particulate reference to certain preferred embodiments thereof, but it will be understood that variations and modifications can be effected within the spirit and scope of the invention.

I claim:

1. A method of medical x-ray diagnostic imaging the blood pool, liver, spleen, or lymph system of a mammal comprising administering to the mammal a contrast effective amount of a mixed carbonic anhydride contrast agent having the structure

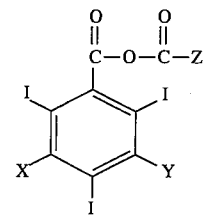

wherein
X is H, $NR^1R^2$ or $CONR^1R^3$,
$R^1$ is H or alkyl,
$R^2$ is $COR^3$,
$R^3$ is H, alkyl or aryl,
Y is $NR^1R^2$ or $CONR^1R^3$, and
Z is alkyl.

2. The method of claim 1 wherein Z is alkyl containing from 1 to 20 carbon atoms.

3. The method of claim 1 wherein X and Y are $NHCOCH_3$.

4. A compound having utility as a contrast agent and having the structure

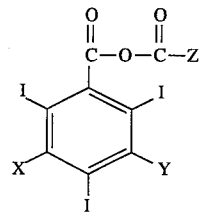

wherein
X is H, $NR^1R^2$ or $CONR^1R^3$,
$R^1$ is H or alkyl,
$R^2$ is $COR^3$,
$R^3$ is H, alkyl or aryl,
Y is $NR^1R^2$ or $CONR^1R^3$, and
Z is $C_2$ to $C_{20}$ alkyl.

5. The compound of claim 4 wherein X and Y are $NHCOCH_3$.

6. An x-ray contrast composition comprising the compound having the structure

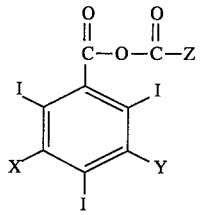

wherein
X is H, $NR^1R^2$ or $CONR^1R^3$,
$R^1$ is H or alkyl, $R^2$ is $COR^3$,
$R^3$ is H, alkyl or aryl,
Y is $NR^1R^2$ or $CONR^1R^3$, and
Z is $C_2$ to $C_{20}$ alkyl.

7. The x-ray contrast composition of claim 6 wherein X and Y are $NHCOCH_3$.

* * * * *